United States Patent [19]

Govindaraju

[11] 4,351,643

[45] Sep. 28, 1982

[54] METHOD FOR CONCENTRATING A LOW-CONCENTRATION ELEMENT IN A SOLUTION

[75] Inventor: Kuppusami Govindaraju, Houdemont, France

[73] Assignee: Instruments S.A., Paris, France

[21] Appl. No.: 160,422

[22] Filed: Jun. 17, 1980

[30] Foreign Application Priority Data

Jun. 18, 1979 [FR] France .................................. 79 15571

[51] Int. Cl.³ ..................... G01N 31/04; G01N 33/24; G01N 33/18; G01J 3/30
[52] U.S. Cl. ............................. 23/230 EP; 23/230 R; 23/230.6; 210/682; 210/688; 422/69; 422/71; 356/316
[58] Field of Search ............ 23/230 R, 230.6, 230 EP; 422/70, 69, 71; 210/670, 682, 688, 681, 662; 356/316

[56] References Cited

U.S. PATENT DOCUMENTS

| | | | |
|---|---|---|---|
| 2,914,378 | 11/1959 | Kennedy | 210/670 X |
| 3,694,369 | 9/1972 | Orlandini | 210/682 X |
| 3,759,617 | 9/1973 | Barringer | 356/316 X |
| 3,915,642 | 10/1975 | Small et al. | 422/69 X |
| 3,967,932 | 7/1976 | Sano et al. | 422/70 X |
| 4,017,262 | 4/1977 | Small et al. | 422/70 X |
| 4,142,858 | 3/1979 | Acuff | 422/70 |
| 4,176,158 | 11/1979 | Laidler et al. | 210/682 X |
| 4,225,314 | 9/1980 | Macourt | 356/316 X |

FOREIGN PATENT DOCUMENTS

646251  2/1979  U.S.S.R. .............................. 422/71

*Primary Examiner*—Kenneth M. Schor
*Attorney, Agent, or Firm*—Pollock, Vande Sande & Priddy

[57] ABSTRACT

Method of concentrating a low-concentration element in a solution and removing other, high-concentration elements, using an ion exchange resin specific to the element to be concentrated.

The resin is disposed in a mini-column less than 3 mm in diameter into which the solution is made to pass, the elution of the element from the resin is carried out by using a very small volume of elution liquid.

The invention applies to quantitative analysis by emission spectrum in an inductive plasma, and in this case the whole of the small volume of elution liquid, previously nebulized, is simultaneously supplied to the plasma.

8 Claims, No Drawings

METHOD FOR CONCENTRATING A LOW-CONCENTRATION ELEMENT IN A SOLUTION

BACKGROUND OF THE INVENTION

The present invention is concerned with a method of concentrating a low-concentration element or group of elements in a solution with a view to their quantitative analysis, for example by emission spectrometry with an inductive plasma excitation source.

In an apparatus for analysis by emission plasma-spectrometry of an element in solution, the solution is supplied to a nebulizer where it is transformed into an aerosol. The aerosol is then introduced into an inductive plasma source where it is excited and emits radiation characteristic of the elements contained in the solution. This radiation is dispersed into spectra in a spectrometer, and a spectral line characteristic of each element to be quantitatively analysed is measured. The intensity measured is proportional to the concentration of the element.

Practical difficulties are encountered in such an analysis technique when the solution studied, or the sample put in solution in advance, contains a high-concentration element or group of elements, often termed "matrix", when other extremely low-concentration elements are the object of interest. This is the case, for example, when quantitative analysis is required of elements such as lead, iron or copper in seawater, in which the concentration of these elements as traces can be a few ppt (part per trillion) whereas the sodium chloride content is of the order of 3%.

This is also the case for the quantitative analysis of elements such as uranium in a rock, in which high concentrations of silicon, aluminum, iron, calcium, magnesium, sodium and potassium are found.

In such instances, the emission of lines is affected by the chemical composition of the matrix. As a result, the spectral background produced by the matrix varies according to the type of sample to be analysed. In such circumstances, with a very low-concentration element, the signal emitted which is recorded in the form of a peak in a traced curve, does not stand out distinctly and clearly but often remains confused with the background. In other words, the signal to background ratio is not sufficiently high to be measured reliably. On the other hand, one or several elements of the matrix can cause spectral interference, for example, interference by iron and calcium in the quantitative analysis of uranium in a rock.

It therefore became necessary to discover a method of concentrating the element in question and the ion exchange technique was used to achieve this. But in current practice this technique is generally used to separate one element concerned and not to enrich it. For separation by ion exchange, a glass column 1 to 3 cm in diameter is generally used, filled with resin up to heights of 10 to 50 cm; a significant volume of solution is made to pass through the column for a first stage of fixing the element in question; for the following elution stage, a significant volume of solution of an elution agent is made to pass through. At the end of the procedure, the element concerned is separated but is found in a significant volume of concentration. To concentrate it, this solution has to be evaporated until dry and the residue dissolved with a minimum volume of solution. The residue can contain salts introduced by the elution agent, for example $NH_4Cl$, which can extend and complicate the evaporation stage. All these procedures make continuous or sequential analyses practically impossible.

SUMMARY OF THE INVENTION

The present invention overcomes these disadvantages and is applied firstly to simultaneously ensure, in a sample of solution, the concentrating of a very low-concentration element, and the removal of a high-concentration element or group of elements, by passing the solution through a column of ion exchange resin for specific fixing of the element in question, and subsequent elution of the element from the resin. According to the invention, the resin is disposed in a column of small diameter, 1 to 3 mm, to a height of 1 to 10 cm, and a small volume of elution agent is then used.

The invention has been developed particularly for quantitative analysis by inductive plasma emission spectrometry. In this instance, the element in question is first concentrated in a column according to the method described above; all of the elution liquid is then introduced directly into the plasma, so that the all of the element contained in the initial sample of the solution enters the plasma at once and takes part in the excitation and emission of the spectrum by the plasma source.

EXAMPLES

The invention will be better understood by reference to two examples of application given hereinafter.

EXAMPLE 1

Quantitative analysis of copper in seawater

A mini-column constituted by a plastic tube of internal diameter of about 2.5 mm, for example of polyvinyl chloride, is used, in which an ion exchange resin specific to copper, for example a complexing resin sold under the trade mark Chelex 100 (200–400 mesh) is disposed; the resin is kept in place in the tube by two glass wool plugs, the bed of resin being 10 cm long.

200 $cm^3$ of seawater, previously treated and brought to pH 7 if necessary, is caused to pass through, by means of a conventional peristaltic pump disposed between the sample-carrier and the mini-column; the column is then rinsed with distilled and de-mineralized water. The copper contained in the sample is fixed on the resin but the sodium of the seawater is removed as waste.

The mini-column is connected to the capillary of the nebulizer of the analysis apparatus and elution of the copper is then carried out with 5 N hydrochloric acid by means of a peristaltic pump. It will then be observed that only 1 ml of acid is required to totally elute the copper previously contained in the 200 $cm^3$ of the sample, which corresponds to a concentration factor of 200. With this concentration and with elimination of the predominant sodium element of the matrix, the peak recorded on the curve traced by the apparatus is distinct, so allowing quantitative analysis of the copper to 1 ppt. It will also be noted that several other bi-valent elements such as lead, nickel, cadmium, zinc, cobalt, and manaqanese are eluted at the same time as the copper, which allows a deferred or simultaneous quantitative analysis of these elements to be envisaged.

EXAMPLE 2

Quantitative analysis of uranium in a silicated rock

The sample of rock is resolved by melting in lithium borate. 500 mg of the product of the melting is put into solution with 50 cm$^3$ of hydrochloric acid (1 N) plus 1 g of ascorbic acid. The final solution is adjusted to pH 3.

A mini-column of the same dimensions as in Example 1 is prepared but with a resin sold under the trade mark Amberlite CG 50 (200-400 Mesh). The column is treated with 10 cm$^3$ of a solution of hydrochloric acid containing 2% of ascorbic acid, adjusted to pH 3 (rinsing solution). The 50 cm$^3$ of solution is then passed through the mini-column by means of a peristaltic pump. The column is rinsed with the rinsing solution at pH 3. In these working conditions, the uranium remains on the resin, the matrix being completely removed.

After the mini-column is connected to the capillary of the nebulizer of an inductive plasma emission spectrometer, the column is eluted with 5 N hydrochloric acid for quantitative analysis of the uranium. The limit of quantitative analysis is 1 ppm, the normal range of the quantitative analysis being 1 to 30 ppm.

It can be observed from these examples that this method lends itself particularly well to multi-element analyses of a single sample, or sequential analysis of several samples. Use of mini-columns in fact allows the initial sample to be divided up so as to be distributed in parallel to several mini-columns grouped in parallel on a single column-carrier, each mini-column being then equipped with a resin specific to one or other of the elements required to be quantitatively analysed. Several mini-columns could also be arranged in parallel and equipped with the same resin but each supplied from different samples by means of the same peristaltic pump.

Each group of mini-columns thus activated in parallel can therefore, after mounting on the spectrum analyser, give rise easily to sequential elution operations, since transfer into the plasma of the whole of the element recovered by one column is done at one time for each column. The result in the form of the analyser diagram will consequently represent either the concentration of each element in question successively or the concentration of one element in a series of samples.

The invention is of course not limited merely to the embodiments described by way of example but also covers embodiments which would differ only in detail, variants of execution or use of equivalent means.

It has thus been possible to establish that the results described hereinbefore are obtainable as long as the column containing the resin has a sufficiently small internal diameter, 1 to 3 mm in practice, the height of the resin in the column being then 1 to 10 cm.

Moreover, the actual method of concentrating can also be applied with other excitation sources used in emission spectrometry, in atomic absorption, spectrometry, spectrophotometry, spectrofluorometry, and X-fluorescence spectrometry. It can also be used to enrich the solution in the element in question, or for recovery of this element.

What I claim is:

1. A method for the quantitative analysis of a first element present in low concentration in a first solution wherein said first solution also contains a second element or group of second elements in a concentration higher than the concentration of said first element which comprises:

passing said solution through a column of ion exchange resin for fixing specifically said first element, wherein the diameter of said column is 1 to 3 mm, and the height of said column is 1 to 10 cm, thereby removing said second element or a group of second elements from said first element;

passing a small volume of elution liquid through said column to elute said first element from the ion exchange resin and thereby obtaining a second solution of said first element wherein said first element is present in higher concentration than in said first solution;

supplying all of said second solution to a nebulizer, thereby transforming said second solution into an aerosol;

introducing all of said aerosol and thereby introducing all of said first element initially present in said first solution into an inductive plasma; and analyzing the spectrum emitted whereby all of the said first element intially present in said first solution takes part in the emission of the spectrum.

2. The method of claim 1 wherein several of said columns are arranged in parallel and wherein a solution is passed to each of the columns and wherein the solutions are analyzed sequentially.

3. The method of claim 2 wherein the columns contain the same ion exchange resin and whereby the concentration of the same element is analyzed for each of the solutions.

4. The method of claim 2 wherein different columns contain different ion exchange resins being specific to different elements present in low concentration, and whereby the concentrations of different elements are analyzed.

5. The method of claim 1 wherein said first element is copper and said first solution is seawater.

6. The method of claim 1 wherein the concentration of uranium in silicated rock is analyzed.

7. The method of claim 5 wherein about 1 ml of an elution liquid is employed.

8. The method of claim 6 wherein about 10 ml of an elution liquid is employed.

* * * * *